United States Patent [19]

Taneda et al.

[11] 3,950,361

[45] Apr. 13, 1976

[54] PROCESS FOR PURIFYING BETA-LACTONES

[75] Inventors: Yasuo Taneda; Tadakazu Tsutada, both of Hino, Japan

[73] Assignee: Teijin Ltd., Osaka, Japan

[22] Filed: July 12, 1971

[21] Appl. No.: 161,979

[30] Foreign Application Priority Data

July 14, 1970 Japan................................. 45-61621

[52] U.S. Cl. ............................................. 260/343.9
[51] Int. Cl.² ....................................... C07D 305/12
[58] Field of Search ................................. 260/343.9

[56] References Cited
UNITED STATES PATENTS 2,759,003   8/1956   Jansen et al. ..................... 260/343.9

FOREIGN PATENTS OR APPLICATIONS 1,954,719   5/1970   Germany ......................... 260/343.9

Primary Examiner—R. Gallagher
Assistant Examiner—Anne Marie T. Tighe
Attorney, Agent, or Firm—Sherman & Shalloway

[57] ABSTRACT

A process for purifying beta-lactones, which comprises contacting a beta-lactone selected from the group consisting of alpha, alpha-dimethyl-beta-propiolactone, beta-propiolactone and a mixture of these with a solid alkaline earth metal hydroxide.

4 Claims, No Drawings

PROCESS FOR PURIFYING BETA-LACTONES

This invention relates to a process for purifying beta-lactones.

Beta-lactones are useful materials for the production of high-molecular-weight compounds by polymerization, yielding fibers, films, plastics, and other fabricated articles. In order to produce high-molecular-weight compounds having a high degree of polymerization, it is necessary to purify beta-lactones to a high degree.

One of the previous methods of purifying beta-lactones is described in French Pat. No. 1,341,074 which discloses the distillation of beta-lactones in the presence of toluylene diisocyanate. This method, however, need be repeated several times in order to obtain beta-lactones of high purity, or requires the step of recovering toluylene diisocyanate. This constitutes an economical defect of the method.

British Pat. No. 1,122,939 discloses a process for purifying alpha, alpha-dimethyl-beta-propiolactone which comprises intimately mixing an organic solvent solution containing 15 % or less of alpha, alpha-dimethyl-beta-propiolactone with an aqueous medium rendered alkaline to a pH of 8 – 13 by hydroxides or carbonates of one or more alkali or alkaline earth metals or ammonium compounds at 5° to 95°C., subjecting the mixture to phase separation and removing the aqueous phase, mixing the lactone phase with demineralized water, and then subjecting the mixture to phase separation and removing the aqueous phase. This process is intended to extract alpha,alpha-dimethyl-beta-propiolactone with alkaline water to remove the impurities, and in order to maintain the water alkaline, an alkaline compound such as salts of alkali metals or alkaline earth metals or ammonium salts is added. This process thus requires a very troublesome operation, and a great quantity of water must be used to treat the compound. Moreover, since alpha,alpha-dimethyl-beta-propiolactone comes into contact with alkaline water, it is considerably hydrolyzed, and there is a great loss of alpha, alpha-dimethyl-beta-propiolactone. Further defects of this process are that fully satisfactory purifying effects are not obtained, and the polymerization or the beta-lactone so purified takes a considerably long time and polymers of satisfactory degrees of polymerization cannot be obtained.

An object of the present invention is to provide an improved process for purifying beta-lactones, which is free from the above-mentioned disadvantages, especially a process whereby highly purified beta-lactones capable of being polymerized to high-molecular-weight polymers within a short time can be recovered in almost quantitative yields rapidly by a simple procedure.

According to the invention, a process is provided for purifying beta-lactones which comprises contacting a beta-lactone selected from the group consisting of alpha,alpha-dimethyl-beta-propiolactone (pivalolactone), beta-propiolactone, and a mixture of these with a solid alkaline earth metal hydroxide.

The hydroxides of alkaline earth metals should be solid. The critical feature of the process of the present invention is that a beta-lactone is contacted with a solid alkaline earth metal hydroxide, and in this respect, the process of the invention is clearly distinguishable from the process disclosed in the British Pat. No. 1,122,939 mentioned above. The method of the present invention might be said to be a method whereby the impurities are adsorbed by the solid alkaline earth metal hydroxide, whereas the above-mentioned British Patent concerns a method of extracting impurities using an alkaline aqueous solution and pure water. Based on this difference, the removal of the impurities is performed more effectively by the process of the present invention than by the process of the British Patent. Accordingly, the beta-lactones purified by the process of the invention can be polymerized to polymers of high intrinsic viscosities within a short period of time.

Examples of the alkaline earth metal hydroxides that are used in the present invention include beryllium hydroxide, magnesium hydroxide, calcium hydroxide, strontium hydroxide and barium hydroxide, the barium hydroxide and strontium hydroxide being especially preferred. These hydroxides may be used alone or as admixtures. It is preferred that the amount of the alkaline earth metal hydroxide should be at least 0.1% by weight based on the beta-lactone to be purified. Strontium hydroxide or barium hydroxide has 1 to 8 moles of water of crystallization, but solid alkaline earth metal hydroxides having water of crystallization are also used with good results in the present invention. Especially, strontium hydroxide or barium hydroxide having 8 moles of water of crystallization can be readily filtered off after mixing with the beta-lactone, and give very good purification effects.

The alkaline earth metal hydroxides to be used in the process of the present invention should not be in the form of solution. For example, strontium hydroxide and barium hydroxide are well soluble in water, but an aqueous solution of these hydroxides is no longer effective in the process of the invention. Stabilizers, flocculating agents, organic solvents, water, and the like may be present during the process of the present invention to an extent such that they do not interfere with the effects of the present invention and the alkaline earth metal hydroxide is present in a solid state. Therefore, the alkaline earth metal hydroxide may be added to crude hydrous beta-lactone, or the alkaline earth metal hydroxide containing adsorbed water may be brought into contact with the beta-lactone. Or it is possible to contact the beta-lactone with the alkaline earth metal hydroxide in the presence of a solvent.

When the alkaline earth metal hydroxide contains a great quantity of free water besides water of crystallization, the hydrolysis of the beta-lactone occurs which not only results in a markedly decreased yield of the purified beta-lactone, but also adversely affects the polymerization of the beta-lactone by an acid produced by the hydrolysis. It is preferred that besides water of crystallization, no free water should be present. However less than 100 %, preferably less than 10 %, based on the weight of the alkaline earth metal hydroxide (including water of crystallization having a maximum coordination number in a stable condition), of free water may be present.

The alkaline earth metal hydroxide should preferably be mixed in the form of finely divided particles in order to enhance the effect of contact between the beta-lactone and the alkaline earth metal hydroxide. In an alternative embodiment of the process of the invention, the beta-lactone is passed through a column packed with finely divided particles of the alkaline earth metal hydroxide. The upper limit of the amount of the solid hydroxide of the alkaline earth metal is not critical, but usually, its amount is 0.1 to 20 % by weight, preferably 1 to 5 % by weight.

The temperature at which the beta-lactone comes into contact with the alkaline earth metal hydroxide is not critical either, but should be restricted to temperatures at which the polymerization of the beta-lactone does not occur, usually 80° to 90°C. The upper limit of this temperature differs depending upon the type of the alkaline earth metal, but for example, it is about 60°C. for magnesium, and about 80°C. for calcium. In the case of barium, it is about 55° to 60°C. although differing according to the number of water molecules of crystallization, and it is about 70°C, in the case of strontium.

The contacting time somewhat varies according to the type of the alkaline earth metal hydroxide, its amount, its particle size, and the contacting temperature, but is preferably above 1 minute. Generally, better results appear to be obtainable by effecting the contacting at higher contact temperatures for short periods of time.

The process of the present invention is practised by mixing a beta-lactone with an alkaline earth metal hydroxide, stirring or refluxing the mixture, if desired under heating, to effect the contacting, and then distilling the mixture. Alternatively, the process is carried out by contacting the beta-lactone with the alkaline earth metal hydroxide, separating the beta-lactone from the alkaline earth hydroxide by such a procedure as filtration, and then distilling the beta-lactone separated. In still another embodiment of the process of the invention, the process of the invention is carried out by passing the beta-lactone through a column packed with the alkaline earth metal hydroxide, and then distilling the beta-lactone.

Still alternatively, the process of the present invention is carried out by dissolving a beta-lactone in an inert solvent not reactive with the beta-lactone, and contacting the resulting solution with an alkaline earth metal hydroxide. The inert solvents that can be used at this time include, for example, halogenated hydrocarbons such as chloroform, dichloroethane, trichloroethylene, or methylene chloride, aromatic hydrocarbons such as benzene or toluene, aliphatic hydrocarbon such as n-hexane, and aromatic ketones such as acetophenone.

The beta-lactone to be purified by the process of the present invention may be produced by any customary method. For instance, alpha,alpha-dimethyl-beta-propiolactone obtained by neutralizing chloropivalic acid with an aqueous alkaline solution, for example an aqueous sodium-hydroxide solution is extracted with an organic solvent, for example chloroform, and then concentrated. Crude beta-lactone obtained can be subjected to the process of the present invention as such.

As mentioned above, according to the process of the present invention, beta-lactones of high purity can be obtained in high yields and at sufficiently high rates by a simpler procedure than those used previously.

The beta-lactones purified by the process of the present invention hardly contain impurities which may adversely affect the polymerization of beta-lactones. By polymerizing the beta-lactones, it is possible to readily produce poly(beta-lactone) of very high-molecular-weight.

The following Examples will illustrate the present invention in greater detail.

EXAMPLES 1 TO 3 AND COMPARATIVE EXAMPLE 1

Three moles of chloropivalic acid were neutralized with an equivalent of an aqueous solution of sodium hyroxide, and 800 ml. of chloroform was added. The reaction were performed for 30 minutes at 40°C. The organic phase was removed by decantation, and to the aqueous phase a fresh supply of chloroform (800 ml) was added; and the reaction was continued for an additional 30 minutes. The organic phase was again removed. The solvent was removed by distillation from the organic phase, followed by distillation under reduced pressure to form alpha,alpha-dimethyl-beta-propiolactone (moisture content 10 mg/100 cc). To 200 g of the resultant crude alpha,alpha-dimethyl-beta-propiolactone 3 % by weight based on the weight of the beta-lactone of calcium hydroxide was added. The mixture was stirred for the contact time indicated in Table 1 below, and distilled at a pressure of 15 mm of Hg. Purified alpha,alpha-dimethyl-beta-propiolactone was recovered in 99 % yield in each run.

For comparison, the crude alpha,alpha-dimethyl-beta-propiolactone was directly distilled under reduced pressure to recover alpha,alpha-dimethyl-beta-propiolactone. As is disclosed in French Pat. No. 1,341,074, the impurities present in a beta-lactone constitute an important factor in polymerizing the lactone to a high-molecular-weight product, and it has been demonstrated that the molecular weight of the resulting polymer varies with the amounts of the impurities. Therefore, in the following Examples, the molecular weight of the polymer after polymerization was determined by the measurement of its intrinsic viscosity, and used as a measure of the purity of the purified beta-lactone.

Fifty grams of the resulting alpha,alpha-dimethyl-beta-propiolactone were dissolved in 200 ml. of hexane, and the solution was put into a 500 ml. three-necked flask. As a catalyst, 0.0001 mole of tetrabutyl ammonium pivalate was added, and the polymerization was performed for 2 hours at 69°C.

The resulting polymer was dissolved in a mixed solvent consisting of 4 parts of o-chlorophenol and 6 parts of phenol, and its intrinsic viscosity was calculated from the value measured at 30°C. in such mixed solvent.

The contact time and the intrinsic viscosity of the resulting polymers are shown in Table 1 below.

Table 1

| Examples | Contact time (hour) | Intrinsic viscosity |
| --- | --- | --- |
| 1 | 1 | 2.60 |
| 2 | 5 | 3.25 |
| 3 | 10 | 3.50 |
| Comp. Ex. 1 | -- | 0.20 |

COMPARATIVE EXAMPLE 2

One hundred grams of the crude alpha,alpha-dimethyl-beta-propiolactone used in Example 1 were dissolved in 2 liters of 1,2-dichloroethane. Two liters of this solution were introduced into a 5-liter steel vessel and intimately contacted by vigorous stirring with 0.4 liter of a solution comprising 2 % by weight of sodium carbonate in water. This solution had a pH of 11.

The stirring was continued for 10 minutes at 20°C. after which the mixture or organic and aqueous media was allowed to settle during a period of 15 minutes. The aqueous phase was removed, and the organic layer was vigorously stirred with 0.4 liter of demineralized neutral water containing in total less than $1 \times 10^{-3}$ % by weight of alkali metal compounds and less than $0.3 \times 10^{-3}$ % by weight of alkaline earth metal compounds, each of these percentages being calculated as weight of metal based on the weight of water. This mixing was effected at 20°C. in the course of 10 minutes. After settling the mixture and removal of the aqueous phase this treatment with demineralized water was repeated once under identical conditions.

After the last settling and removal of the aqueous phase, alpha,alpha-dimethyl-beta-propiolactone was recovered from the organic solution by distilling off the organic solvent at atmospheric pressure and at a temperature which was gradually increased from the normal boiling point (83.5°C.) to higher values in order to remove the last amounts of organic solvent. This distillation was effected in the presence of 15 g of picric acid.

Subsequent to the removal of dichloroethane, the lactone was subjected twice to distillation at 70 to 20 mm of Hg respectively, to remove compounds having a lower and higher boiling point than the lactone.

The yield of the purified alpha,alpha-dimethyl-beta-propiolactone was 70 g.

In the same way as set forth in Example 1, the lactone was polymerized for 2 hours at 69°C. using n-hexane as a solvent. The yield of the polymer was 98 %, and the polymer had an intrinsic viscosity of only 1.2.

EXAMPLES 4 TO 9

The crude alpha,alpha-dimethyl-beta-propiolactone used in Example 1 was put in portions in six vessels provided with a stirrer. On the other hand, barium hydroxide [$Ba(OH)_2.8H_2O$] was dried at 90°C. for 5 hours under reduced pressure. The powders of the barium hydroxide obtained were added in an amount of 1 % by weight to three vessels, and in an amount of 3 % by weight to the remaining three vessels, the percentages being based on the beta-lactone. The mixture was stirred at 25°C. for 1, 5, and 20 hours respectively according to the schedule shown in Table 2. The solid matter was removed by filtration, and then 0.1 % by weight of gamma-resorcylic acid was added on the basis of alpha,alpha-dimethyl-beta-propiolactone. The distillation was performed at reduced pressure at a rate of 200 ml. per hour.

In the same way as set forth in Example 1, the polymerization of the purified beta-lactone was performed for 2 hours at 69°C. using n-hexane as a solvent and 0.02 mole %, based on the monomer, of a catalyst. The results are shown in Table 2 below.

Table 2

| Examples | Amount of barium hydroxide added (wt. %) | Stirring time (hr) | Yield of purified lactone (%) | Yield of polymer | intrinsic viscosity |
|---|---|---|---|---|---|
| 4 | 1 | 1 | 99.0 | quantitative | 2.4 |
| 5 | 1 | 5 | 99.0 | " | 3.0 |
| 6 | 1 | 20 | 98.5 | " | 4.8 |
| 7 | 3 | 1 | 99.0 | " | 2.6 |
| 8 | 3 | 5 | 99.0 | " | 3.4 |
| 9 | 3 | 20 | 98.0 | " | 5.1 |

EXAMPLE 10

Three moles of chloropivalic acid were neutralized with an equivalent of an aqueous solution of sodium hydroxide. Chloroform (800 ml.) was added, and the reaction was performed for 30 minutes at 40°C. The organic phase was removed by decantation and to the aqueous phase a fresh supply of chloroform (800 ml.) was added and the reaction was continued for an additional 30 minutes. The organic phase was again removed, and the organic phase was concentrated at reduced pressure to an alpha,alpha-dimethyl-beta-propiolactone content of about 40 % by weight. To the concentrated liquid 2 % by weight of barium hydroxide (the dry barium hydroxide described in Example 4) was added, and the mixture was stirred for 30 minutes at 50°C. The solid matter was removed by filtration, and then alpha,alpha-dimethyl-beta-propiolactone was fractionally distilled. The yield of the purified lactone was 95.4 %. In order to determine its purity, 50 g of alpha,alpha-dimethyl-beta-propiolactone were dissolved in 200 ml. of come commercial grade n-hexane, and the solution was placed in a 500 ml. of separable flask. With stirring, 0.02 mole % (based on the beta-lactone) of tetrabutylammonium pivalate was added, and the polymerization was performed for 2 hours at 69°C. The conversion was 100 %, and the intrinsic viscosity of the polymer was 2.8.

EXAMPLE 11

Crude alpha,alpha-dimethyl-beta-propiolactone used in Example 1 was continuously passed through a cylindrical column having an inner diameter of 10 mm and a length of 50 cm and held at 50°C., which column had been packed with barium hydroxide (particle size 50 to 300 microns) dried for 5 hours at 90°C. and reduced pressure. The residence time of the beta-lactone in the column was from 10 to 15 minutes. The separated beta-lactone was distilled at 50°C. with the addition of 0.1 % by weight of gamma-resorcylic acid. The yield of the purified beta-lactone was 94 %. The beta-lactone so purified was polymerized in the same way as set forth in Example 1, and then its viscosity was measured. It was found that the polymer had an intrinsic viscosity of 2.7.

EXAMPLE 12

200 g of the crude alpha,alpha-dimethyl-beta-propiolactone used in Example 1 together with 2 g of magnesium hydroxide were mixed and stirred for 5 hours at 30°C. The solid matter was removed by filtration, and then on addition of 0.1 % by weight of gamma-resorcylic acid, the beta-lactone was distilled at 50°C. under reduced pressure. The yield of the purified beta-lactone was 90 %. The resulting alpha,alpha-dimethyl-beta-propiolactone was polymerized in the same manner as shown in Example 1. The polymer obtained had an intrinsic viscosity of 3.0.

EXAMPLE 13 AND COMPARATIVE EXAMPLE 3

Two hundred grams of beta-propiolactone (first grade reagent, product of Tokyo Chemical Industry) were stirred for 5 hours at 30°C. together with 6 g of calcium hydroxide. The solid matter was removed by filtration, and at a reduced pressure of 15 mm of Hg, beta-propiolactone was distilled. The yield of the purified beta-lactone was 85 %.

Thirty grams of the purified beta-propiolactone were dissolved in 100 ml. of toluene, and on addition of 0.1 mole % of carboxymethyl trimethyl ammonium hydroxide anhydride, the reaction was performed for 50 hours at 0°C. with stirring. The resulting polymer had an intrinsic viscosity of 2.3.

For comparison, untreated beta-propiolactone was distilled at a reduced pressure of 15 mm of Hg. The yield of the purified beta-lactone was 87 %. The purified beta-lactone was polymerized in the same manner as described above. The resulting polymer had an intrinsic viscosity of 1.2.

EXAMPLE 14

One hundred grams of strontium hydroxide [$Sr(OH)_2.8H_2O$] were dried at 70°C. for 4 hours to form 78 g of dried strontium hydroxide. To the crude alpha,alpha-dimethyl-beta-propiolactone used in Example 1 were 4 % by weight, based on the beta-lactone, of the dried strontium hydroxide was added. The mixture was stirred for 10 minutes at 50°C. to effect intimate contact. The solid matter was removed. On addition of 0.1 % by weight of gamma-resorcylic acid, the treated alpha,alpha-dimethyl-beta-propiolactone was distilled at a reduced pressure of 15 mm of Hg. The yield of the alpha,alpha-dimethyl-beta-propiolactone recovered was 98 %. The beta-lactone was polymerized in the same way as set forth in Example 1. The yield of the polymer was quantitative, and the intrinsic viscosity of the polymer was found to be 3.10.

COMPARATIVE EXAMPLE 4

Three grams of sodium hydroxide were added to 100 g of crude alpha,alpha-dimethyl-beta-propiolactone used in Example 1, and the mixture was stirred at 50°C. Polymerization proceeded gradually, and the liquid became whitely turbid. In about 9 minutes, the entire system became a slurry, and finally it solidified. This demonstrated that the use of an alkali metal hydroxide induced the polymerization of beta-lactone during its purification step, and thus is not suitable.

COMPARATIVE EXAMPLE 5

Three grams of calcium oxide in powder form were added to 100 g of the crude alpha,alpha-dimethyl-beta-propiolactone used in Example 1, and the mixture was stirred for 10 minutes at 50°C. The solid matter was then removed by filtration using a glass filter. To the filtrate 0.1 % by weight of gamma-resorcylic acid was added, and the distillation was carried out at a reduced pressure of 15 mm of Hg. The yield of the purified alpha,alpha-dimethyl-beta-propiolactone was 99 %. The purified beta-lactone was polymerized in the same way as set forth in Example 1. The yield of the polymer was 95 %, and the intrinsic viscosity of the polymer was 0.6.

EXAMPLES 15 TO 21 AND COMPARATIVE EXAMPLES 6 AND 7

One hundred grams of barium hydroxide [$Ba(OH)_2.8H_2O$] were dried under various conditions to a weight of 60.0 g (to be referred to as A), 71.5 g (to be referred to as B), 85.0 g (to be referred to as C), and 94.5 g (to be referred to as D). Non-dried barium hydroxide was designated as E.

Water was added to the undried barium hydroxide (E). A mixture of 100 g of E with 10 g of water was designated as F, and a mixture of 100 % of E with 100 g of water, as G.

On the other hand, using the undried barium hydroxide (E), a saturated aqueous solution of barium hydroxide at 50°C was prepared and designated as H. A 5 % by weight aqueous solution of the undried barium hydroxide (E) was prepared and designated as I.

To 100 g of the crude alpha,alpha-dimethyl-beta-propiolactone used in Example 1 each of barium hydroxides (A) to (G) and aqueous solutions of barium hydroxide (H) and (I) for comparison was added in the amount indicated in Table 3. The mixture was stirred for 10 minutes at 50°C. The solid matter was removed by filtration, the aqueous phase was decanted and distillation was carried out in the same manner as set forth in Example 4. The purified beta-lactone was polymerized in the same manner as set forth in Example 1, and the intrinsic viscosity of the polymer was measured. The results obtained are shown in Table 3.

Table 3

| Examples | Treating agent | Amount of treating agent (%) | Yield of purified product (%) | Yield of polymer | intrinsic viscosity of the polymer |
|---|---|---|---|---|---|
| 15 | A | 3.0 | 98.5 | quantitative | 2.7 |
| 16 | B | 3.0 | 98.0 | " | 3.0 |
| 17 | C | 4.0 | 97.5 | " | 3.5 |
| 18 | D | 4.0 | 97.5 | " | 3.6 |
| 19 | E | 5.0 | 97.0 | " | 4.0 |
| 20 | F | 5.5 | 95.0 | " | 2.4 |
| 21 | G | 10.0 | 93.2 | " | 2.0 |
| Com. Ex. 7 | H | 30.0 | 82.7 | 95 % | 0.8 |
| Com. Ex. 8 | I | 100.0 | 79.5 | 45 % | 0.3 |

The foregoing results demonstrate that the presence of some water in the purification system does not affect the purification of the beta-lactone, but when the water is present in excess such that the alkaline earth metal hydroxides become aqueous solutions, the purification of beta-lactone is adversely affected.

What we claim is:

1. A process for purifying beta-lactones, which comprises contacting a beta-lactone selected from the group consisting of alpha,alpha-dimethyl-beta-propiolactone, beta-propiolactone and a mixture thereof, with a solid phase alkaline earth metal hydroxide in an amount of from 0.1% to 20% by weight based on the weight of said beta-lactone, in the substantial absence of free water.

2. The process of claim 1 wherein said alkaline earth metal hydroxide is the hydroxide of magnesium, calcium, barium or strontium.

3. The process of claim 1 wherein said beta-lactone is contacted with said alkaline earth metal hydroxide at 10° to 80°C.

4. The process of claim 1 wherein said alkaline earth metal hydroxide is the hydroxide of barium or strontium containing 8 moles of water of crystallization.

* * * * *